United States Patent [19]

Satzinger et al.

[11] 4,002,665

[45] Jan. 11, 1977

[54] PROCESS FOR SUBSTITUTED CYCLOHEXENES AND ITS PRODUCTS

[75] Inventors: Gerhard Satzinger, Gundelfingen; Gustav Hechtfischer, Freiburg-Landwasser, both of Germany

[73] Assignee: Warner-Lambert Company, Morris Plains, N.J.

[22] Filed: Aug. 14, 1973

[21] Appl. No.: 388,285

Related U.S. Application Data

[62] Division of Ser. No. 117,142, Feb. 19, 1971, Pat. No. 3,792,080.

[52] U.S. Cl. .......................................... 260/471 A
[51] Int. Cl.² ..................................... C07C 101/14
[58] Field of Search ............................... 260/471 A

[56] References Cited

UNITED STATES PATENTS

| | | |
|---|---|---|
| 3,882,164 | 5/1975 | Satzinger et al. ............. 260/471 A |
| 3,905,978 | 9/1975 | Satzinger et al. ............. 260/471 A |
| 3,957,851 | 5/1976 | Satzinger et al. ............. 260/471 A |

*Primary Examiner*—Paul J. Killos
*Attorney, Agent, or Firm*—Albert H. Graddis; Frank S. Chow; George M. Yahwak

[57] ABSTRACT

The present invention relates to a process for 3r-N-Monomethylamino-4 cis-phenyl-4 trans-ethoxycarbonyl-cyclohexene and its N-substitution products which are generally useful as analgesics.

11 Claims, No Drawings

PROCESS FOR SUBSTITUTED CYCLOHEXENES AND ITS PRODUCTS

This is a division of application Ser. No. 117,142 filed Feb. 19, 1971, now U.S. Pat. No. 3,792,080.

The present invention relates to a process for the production of 3r-N-monomethylamino-4C-phenyl-4t-ethoxycarbonylcyclohexene-(1) (I) and its N-substitution products of the general formula II

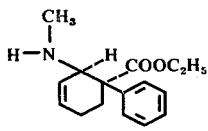
I

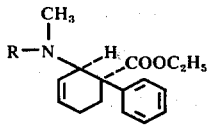
II where R represents a lower alkyl, aralkyl, or alkenyl radical, a substituted lower alkyl or an acyl group, the term "lower alkyl radical" meaning a hydrocarbon radical having 1 to 7 C atoms arranged in a straight or branched chain, the term including radicals such as ethyl, propyl, isopropyl etc. With the "lower substituted alkyl radical" a di-lower-alkyl-amino group has been substituted for a hydrogen atom, in addition; the two lower alkyl radicals may be linked to form a ring either with or without intervention of a heteroatom. The term "aralkyl" means a lower alkyl radical where the phenyl group has been substituted for an H-atom, such as benzyl and phenethyl. The term "alkenyl" signifies an unsaturated hydrocarbon having 3 to 5 C atoms. For the purpose of this specification acid radicals of the category of substituted or non-substituted lower alkane carboxylic acids, aromatic carboxylic acids and carbamic acids, such as acetyl, propionyl, succinoyl, oxalyl, maleyl, benzoyl, aminobenzoyl, chlorobenzoyl, carbamyl, ethylcarbamyl etc, are termed "acyl groups".

This invention also comprises acid addition or quarternary compounds of such products I and II which are capable of forming salts with non-toxic, pharmaceutically acceptable acids or alkyl halides.

Compounds I and II of the invention exhibit considerable analgesic and anti-inflammatory activity in mammals such as mice, rats, dogs etc., as normally used in pharmacological tests. Therapeutic application of these compounds is indicated in use of pain all kinds. The dose required for removing pain is between 5 and 50 mg/kg body weight.

For pharmaceutical use the products of the invention may, when provided with the usual galenic additives, be processed into dosge forms of medical benefit, such as tablets, capsules, ampoules etc.

Compounds II of the invention are prepared by way of I from 3r-N,N-dimethylamino-4c-phenyl-4t-ethoxycarbonyl-cyclohexene(1) (III); preparation of III has been described in my U.S. Pat. No. 3,577,127, issued Jan. 19, 1971.

1. It has now been found, most surprisingly, that 3r-N-

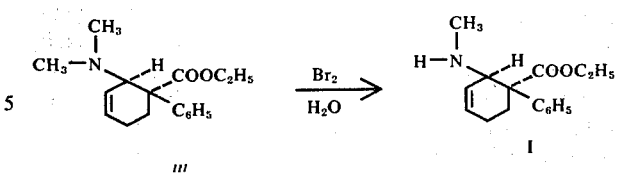

monomethylamino-4c-phenyl-4t-ethoxycarbonyl-cyclohexene-(1) (I), a compound which owing to its strong analgesic activity is of pharmaceutical interest as such and is used as the starting material for the preparation of substances II, can be produced in a most simple way by bromination of III in a carbon chloride, preferably in chloroform, at −15° to 0° C, advantageously at −10° C, and subsequent treatment with water. This reaction is all the more remarkable as it runs without addition of any bromine to the cyclohexene double bond, without allyl bromination and without substitution of the phenyl nucleus. Conventional, multistage de-alkylation procedures like von Braun degradation or degradation by means of acylating agents were found to fail in the preparation of I, resulting merely in an unidentifiable mixture of secondary products. Furthermore preparation of I out of III in small yields is possible by means of oxidation of II with $Hg^{II}$-acetate in aqueous acetic acid at elevated temperatures, preferably the boiling point of 10% acetic acid, and by oxidation of III with gaseous oxygen in the presence of noble metal catalysts, preferably $PtO_2$, in an inert solvent, advantageously in benzene.

2. Compound I can be reacted with alkyl halides, acyl halides, aminoalkyl halides, and isocyanates. These reactions are best illustrated by the following reaction chart:

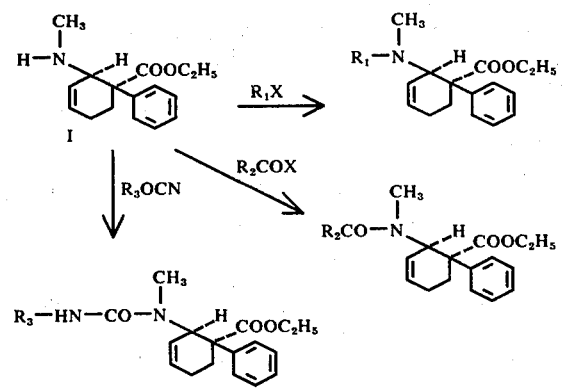

where the groups $R_1$, $R_2CO$, and $R_3NH.CO$ represent a lower, substituted or non-substituted alkyl or alkenyl radical, an acyl radical, or a carbamic acid radical, as defined above.

These known reactions of secondary amines, require a special working technique, owing to the low basicity and the enormous steric hindrance of the N-atom, on the one hand, and the sensitivity of I, on the other hand. For the alkylation reactions in the presence or absence of a solvent, this means that reaction is forced, by using at least an equimolar amount of N-ethyldiisopropylamine as the condensation agent, and observing a temperature range of 70°–130° C. Acylations are also performed by means of this amine or — which is less effective — by triethylamine. This preferred temperature range is between 0 and 100° C. Aromatic hydrocarbons, toluene in particular, have proved to be suitable solvents. Reactions with anhydrides can be achieved by a melting process or in DMF-solution, a temperature range of 120°–140° C having to be observed. Acylation with isocyanates is performed in an ether at 15°–50° C, preferably in dioxane at 30° C. Free cyanic acid in aqueous acetic acid at 70° C adds to the NH group of I.

The following examples are given to illustrate the invention:

1. 3r-N-Monomethylamino-4c-phenyl-4t-ethoxycarbonylcyclohexene-(1) (I)

1.1 To a well stirred solution of 273.3 g. (1 mole) of III in 0.5 l. of chloroform 159.8 (1 mole) of bromine dissolved in 250 cc. of chloroform are added dropwise at −10° C within 90 min. Stirring is continued for 30 min. at −10° C. The solution is poured into 4 l. of water, and the phases are stirred for 5 hours at room temperature. The mixture is rendered alkaline with aqueous ammonia, the organic phase is washed twice with water, dried over $MgSO_4$ and evaporated; the residue is taken up in ethyl acetate, and the hydrochloride of I is precipitated by a solution of hydrogen chloride in ethyl acetate. The product is analytically pure. M.P.: 218°–219° C. It can be recrystallized from a mixture of ethyl acetate and isopropanol. The free base melting between 39.5 and 40.5° C is prepared by alkalizing with aqueous NaOH.

Yield 320 g. (62% as hydrochloride) $C_{16}H_{22}ClNO_2$ (295.9) Calculated: C, 64.94; H, 7.50; N, 4.73; Cl, 11.98. Found: C, 64.74 H, 7.36; N, 4.82; Cl, 12.34.

1.2 108 g. (0.4 mole) of III are dissolved in 1 l. of 10% acetic acid; then a solution of 505 g. (1.6 moles) of $Hg^{II}$-acetate in 2 l. of 10% acetic acid is added and the mixture heated to boiling for 2 hours. The precipitated $Hg^I$ salt is separated, and the filtrate alkalized with 2 N sodium hydroxide solution. The oily portion is taken up in ether; the ethereal phase is evaporated and the residue extracted with petroleum ether. Following evaoration of the solvent, the residue is taken up in ethyl acetate and converted into the hydrochloride as described above.

Yield: 24.0 g. (23.5% of theory) M.P. 212°–213° C.

1.3 13.6 g. (0.05 mole) of III are dissolved in 100 ml. benzene. To this solution 2 g. of $PtO_2$ are added, and the mixture is shaken without pressure in an $O_2$ atmosphere for 8 days. After filtrating, the benzene phase is extracted with 2 N acetic acid and the aqueous layer alkalized with 2 N NaOH. The oil which has separated is taken up in ethyl acetate and converted into the hydrochloride according to 1.2 M.P. 212°–213° C.

Yield: 0.6 g. (4.7%)

2. 3r-(N-Methyl-N-ethyl-amino)-4c-phenyl-4t-ethoxycarbonyl-cyclohexene-(1)

51.8 g. (0.2 mole) of 3r-N-monomethylamino-4c-phenyl4t-ethoxycarbnyl-cyclohexene-(1) (I) are added to 35 g. of diethyl sulfate and 45 g. of N-ethyl-diisopropylamine within 1 h. at 100° C. Subsequently the mixture is heated for another 2 hrs. to 125°–130° C. After cooling, it is mixed with a solution of 0.3 mole of KOH in 30 cc. of water, with stirring, and the separated aqueous phase is extracted with ether. The combined organic layers are dried and freed from ether and amine. The residue is taken up in ethyl acetate. Any starting substance not transformed is precipitated by addition of 200 ml. of a saturated ethereal oxalic acid solution.

From the filtrate, 2 is precipitated as naphthalene-1,5-disulfonate

Yield: 40.0 g. (47%) from isopropanol. M.P. 171°–173° C. $C_{46}H_{58}N_2O_{10}S_2$ (863.12) Calculated: C, 64.01; H, 6.77; N, 3.25; S, 7.44. Found: C, 64.31; H, 6.68; N, 3.18; S, 7.15.

3. 3r-(N-Methyl-N-allyl-amino)-4c-phenyl-4t-ethoxycarbonyl-cyclohexene-(1)

25.9 g. (0.1 mole) of I together with 16 g. of allyl bromide and 22 g. of ethyldiisopropylamine, are heated for 1 h. to 90° C. After cooling, the product is taken up in ether and filtered, the ethereal phase being washed with water and dried over potassium carbonate. The residue of the ethereal phase (at 12 torr, 100° C) is dissolved in isopropanol, a solution of naphthalene-1,5-disulfonic acid in isopropanol being added. The naphthalene-1,5-disulfonate of 3 precipitates.

Yield: 26.2 g. (30%) from isopropanol. M.P. 182°–185° C. $C_{48}H_{58}N_2O_{10}S_2$ (887.1) Calculated: C 64.98 H 6.60 N 3.16 S 7.22 Found: 65.20 6.55 3.24 7.13

4. 3r-(N-Methyl-N-phenethylamino)-4c-phenyl-4t-ethoxycarbonyl-cyclohexene-(1)

51.8 g. (0.2 mole) of I, 45 g. of β-phenethylbromide, and 55 g. of N-ethyldiisopropylamine are dissolved in 300 cc. of dimethylsulfoxide and heated for 3 hrs. to 100° C. This solution is introduced into 1 l. of water; following extraction with toluene the organic phase is evaporated to dryness under vacuum. The residue is taken up in ethyl acetate and freed from the starting material as in example 2. By evaporation and alkalization with 2 N NaO.. the base according to 4. is freed. It is precipitated as naphthalene-1,5-disulfonate when dissolved in isopropanol as in example.

Yield: 15 g. (31%) from a mixture of ethanol and isopropanol. M.P. 172°–173° C. $C_{58}H_{66}N_2O_{10}S_2$ (1015.32) Calculated: C, 68.61; H, 6.55; N, 2.76; S, 6.31. Found: C, 68.44; H, 6.65; N, 2.70; S, 6.43.

5. 3r-(N-Methyl-N-β-morpholinoethyl-amino)-4c-phenyl-4t-ethoxycarbonyl-cyclohexene-(1)

25.9 g. (0.1 mole) of I and 0.1 mole of freshly prepared N-(2-chloroethyl)-morpholine are dissolved in 100 cc. of dimethyl-sulfoxide and, together with 35 g. of N-ethyl-diisopropyl-amine, heated for 6 hrs. to 100° C. The product is taken up in toluene; the organic phase is thoroughly washed with water, dried over $K_2CO_3$ and evaporated. The product of 5 is obtained as oxalate upon addition of an ethyl acetate solution of oxalic acid to the solution of the residue in ethyl acetate.

Yield: 9 g. (18%) from acetonitrile. M.P. 173°–176° C. $C_{24-34}N_2O_7$ (462.55) Calculated: C, 62.32; H, 7.41; N, 6.05. Found: C, 62.14; H, 7.30; N, 5.87.

6. 3r-(N-Methyl-N-tetramethylene-ammonium)-4c-phenyl-4t-ethoxycarbonyl-cyclohexene-(1)-iodide 25.9 g. (0.1 mole) of I, 38 g. of 1,4-diiodobutane, and 25 g. of N-ethyl-diisopropylamine are heated together to 100° C. Subsequently the mixture is stirred for 1 hour at 125° C. The reaction product is extracted twice with boiling toluene, the residue taken up in chloroform, and this solution is washed with aqueous ammonia and water. After distilling off the chloroform, the residue is recrystallized from isopropanol.

Yield: 4.5 g. (10%). M.P. 153°–156° C. $C_{20}H_{28}NIO_2$ (441.36) Calculated: C, 54.42; H, 6.40; I, 28.75; N, 3.18. Found: C, 54.74; H, 6.27; I, 28.78; N, 3.52.

7. 3r-(N-Methyl-N-capryloyl-amino)-4C-phenyl-4t-ethoxycarbonyl-cyclohexene-(1)

To a solution of 25.9 g. (0.1 mole) of I and 22 g. of N-ethyl-diisopropylamine in 300 ml. of toluene 17 g. of capryloyl chloride are added dropwise at a temperature not exceeding 30° C. After 2 hrs. the mixture is stirred for 30 min. at 60° C. The product is washed twice with 2 N hydrochloric acid and once with water, then dried and concentrated at 100° C, 0.4 torr. The residue is analytically pure.

Yield: 32.5 g. (84%). An almost colorless, undistillable oil. $C_{24}H_{35}NO_3$ (385.55) Calculated: C, 74.77; H, 9.15; N, 3.63. Found: C, 74.90; H, 9.24; N, 3.74.

8. 3r-[N-Methyl-N-(4'-chlorobenzoyl)-amino]-4c-phenyl-4t-ethoxycarbonyl-cyclohexene-(1)

To a solution of 25.9 g. (0.1 mole) of I and 16 g. of N-ethyl-diisopropylamine in 700 cc. of toluene, 17.5 g. (0.1 mole) of p-chlorobenzoyl chloride, dissolved in 50 cc. of toluene, are added dropwise, at +5° C. The mixture is allowed to warm to room temperature, and subsequently it is heated for 1 h. to 70° C. The reaction solution is extracted with 2 N hydrochloric acid and water. The residue of the toluene phase is recrystallized from ethanol.

Yield: 30.1 g. (76%). M.P. 175°–177° C. $C_{23}H_{24}ClNO_3$ (397.91) Calculated: C, 69.42; H, 6.08; Cl, 8.91; N, 3.52. Found: C, 69.59; H, 6.15; Cl, 8.95; N, 3.54.

9. 3r-[N-Methyl-N-(2-carboxyethelcarbonyl-amino]-4c-phenyl-4t-ethoxycarbonyl-cyclohexene-(1)

38.8 g. (0.15 mole) of I and 15 g. of succinic anhydride are heated to form a homogeneous melt and kept at 120° C for 3 hrs. The melt is taken up in toluene while hot. The crude product obtained on cooling is recrystallized from ethanol.

Yield: 34.4 g. (62%). M.P. 132°–133° C. $C_{20}H_{25}NO_5$ (359.43) Calculated: C, 66.83; H, 7.01; N, 3.90. Found: C, 66.93; H, 7.06; N, 3.90.

10. 3r-[N-Methyl-N-(2'-amino-benzoyl)-amino]-4c-phenyl-4t-ethoxycarbonyl-cyclohexene-(1)

25.9 g. (0.1 mole) of I are heated to 140° C, and 0.1 mole of isatsic anhydride is introduced in several portions. The mixture is kept at this temperature for 2 hrs. and subsequently taken up in toluene while hot; then the toluene phase is extracted with 0.5 N hydrochloric acid and with 0.5 N sodium hydroxide solution. After being dried, the organic phase is evaporated under vacuum, and the residue crystallized with isopropanol.

Yield: 5.0 g. (13%) from a mixture of isopropanol and diisopropylether. M.P. 138°–140° C. $C_{23}H_{26}N_2O_3$ (378.47) Calculated: C, 72.98; H, 6.93; N, 7.40. Found: C, 72.95; H, 6.78; N, 7.38.

11. N,N'-Dimethyl-N,N'-di[Nr(4c-phenyl-4t-ethoxycarbonyl-cyclohexene-1-yl-3)]succinamide To 38.8 g. (0.15 mole) of I and 33 g. of N-ethyldiisopropylamine, dissolved in 600 cc. of toluene, 12 g. of succinic dichloride are added dropwise at 5°–10° C. The solution is stirred for several hours at room temperature and subsequently heated to 90°–100° C for 2 hrs. On cooling a precipitate is formed, which is then suspended in 0.5 N hydrochloric acid and recrystallized from isopropanol. The yield (including the product obtained from the toluene mother liquor) amounts to 35.4 g. (78%). M.P. 196°–198° C. $C_{36-44}N_2O_6$ (600.77) Calculated: C, 71.97; H, 7.38; N, 4.66. Found: C, 72.06; H, 7.42; N, 4.80.

12. N,N'-Dimethyl-N,N'-di[Nr-(4c-phenyl-4t-ethoxycarbonyl-cyclohexene-1yl-3]oxamide To a solution of 38.8 g. (0.15 mole) of I and 30 g. of triethylamine in 800 cc. of toluene 0.075 mole of oxalic dichloride is added dropwise, at 0° to 5° C. After stirring for 1 hour at room temperature, the precipitate is separated, taken up in chloroform, washed with 2 N hydrochloric acid and finally with water. The residue on distillation is recrystallized from N-butanol.

Yield: 7.7 g. (16%). M.P. 253°–255° C. $C_{34}H_{40}N_2O_6$ (572.71) Calculated: C, 71.30; H, 7.04; N, 4.89. Found: C, 71.25; H, 6.95; N, 4.86.

13. 3r-(N-Methyl-N-carbamyl)-amino-4c-phenyl-4t-ethoxycarbonyl-cyclohexene-(1)

To 13 g. (0.05 mole) of I, dissolved in a mixture of 24 ml. of glacial acetic acid and 20 ml. of water, a solution of 8 g. of potassium cyanate in 10 ml. of water is added at 30° C. The mixture is heated for 45 min. to 70° C, poured into water, and extracted with chloroform. The organic phase is extracted with 2 N HCl and with water. After drying the phase and evaporating, the residue is recrystallized from toluene.

Yield: 2.6 g. (17%). M.P. 142°–144° C. $C_{17}H_{22}N_2O_3$ (302.38) Calculated: C, 67.52; H, 7.33; N, 9.27. Found: C, 67.56; H, 7.42; N, 9.31.

14. 3r-[N-Methyl-N-(ethylcarbamyl)]-amino-4C-phenyl-4t-ethoxycarbonyl-cyclohexene-(1)

0.025 mole of ethylisocyanate and 0.025 mole of I are united in 30 ml. of dioxane and heated for 5 hrs. to 30° C. The residue of the dioxane phase is recrystallized from aqueous isopropanol.

Yield: 5.3 g. (64%). M.P. 140°–141° C. $C_{19}H_{26}N_2O_3$ (330.43) Calculated: C, 69.06; H, 7.93; N, 8.48. Found: C, 69.34; H, 7.78; N, 8.19.

15. 3r-[N-Methyl-N-(butylcarbamyl)]-amino-4c-phenyl-4t-ethoxycarbonyl-cyclohexene-(1)

This compound is prepared from butylisocyanate and I, as in example 14.

M.P. 117°–118.5° C. Recrystallized from isopropanol. $C_{21}H_{30}N_2O_3$ (358.49) Calculated: C, 70.35; H, 8.44; N, 7.82. Found: C, 70.27; H, 8.26; N, 8.02.

16. 3r-[N-Methyl-N-(2'-carboxy-phenyl-carbamylamino)]-4c-phenyl-4t-ethoxycarbonyl-cyclohexene-(1)

51.8 g. (0.2 mole) of I and 0.15 mole of isatoic anhydride are heated in 250 cc. of DMF for 3 hrs. to 110°–20° C. The solvent is distilled off, and after being taken up in toluene the residue is extracted with 500 cc. of 0.5 N hydrochloric acid. This results in the precipitation of the product according to 16.

Yield: 21.8 g. (34%). M.P. 187° C (decomposition) from isopropanol. $C_{24}H_{26}N_2O_5$ (422.48) Calculated: C, 68.22; H, 6.21; N, 6.63. Found: C, 68.22; H, 6.31; N, 6.31.

The analgesic effectiveness and $LD_{50}$ of representative compounds produced by the process of the present inventions were demonstrated in the following tests:

The $LD_{50}$ values were determined using male and female rats with weights in the range of 90 to 120 grams:

3r-N-monomethylamino-4-c-phenyl-4t-ethoxycarbonyl-cyclohexene-(1).

In a test of 12 animals, $LD_{50}$ was determined to be 250 mg/kg when administered subcutaneously and the $LD_{50}$ in intragastric administration was 550mg/kg.

This same compound demonstrated analgesic activity using the phenyl-p-quinone writhing test. Twelve out of twelve rats were protected from sensitivity from pain at a dosage level of 11.25 mg/kg. The compound in this case was administered subcutaneously.

3r-(N-methyl-N-ethyl-amino)-4c-phenyl-4t-ethoxycarbonyl-cyclohexene-(1).

The LD$_{50}$ in the form of an Armstrong salt using the method as above, was determined to be 1600 mg/kg when administered intragastrically.

The LD$_{50}$ of this compound in the form of its oxalate salt was 453 mg/kg administered intragastrically.

In the Randall-Selitto test the following values have been obtained administering the compound in water intragastrically in a dosage of 100 mg/kg.

Control animals are in pain at a load of 148 g. Animals having 100 mg/kg of amidopyrine are in pain at a load of 212 g. Animals treated with the compound of the invention are in pain at a load of 352 g.

Having described our invention, we claim:

1. A compound of the formula:

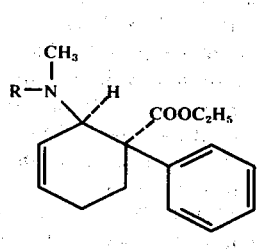

wherein R is selected from the group consisting of

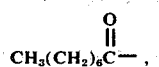

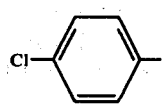

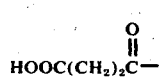

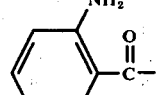

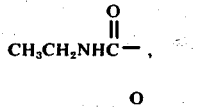

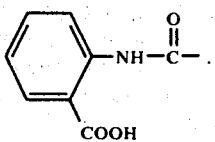

2. The compound of claim 1 wherein R is

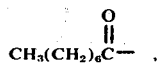

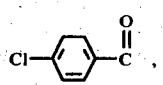

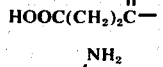

3. The compound of claim 1 wherein R is

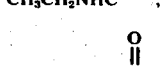, and

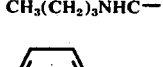

4. A compound as set forth in claim 2 wherein R is capryloyl.

5. A compound as set forth in claim 2 wherein R is 4' chlorobenzoyl.

6. A compound as set forth in claim 2 wherein R is carboxyethylcarbonyl.

7. A compound as set foth in claim 2 wherein R 2'-aminobenzoyl.

8. A compound as set forth in claim 3 wherein R is carbamyl.

9. A compound as set forth in claim 3 wherein R is ethyl carbamyl.

10. A compound as set forth in claim 3 wherein R is butyl carbamyl.

11. A compound as set forth in claim 3 wherein R is 2'carboxyphenyl-carbamyl.

* * * * *